United States Patent [19]

Palumbo

[11] 4,117,554

[45] Oct. 3, 1978

[54] PROTECTIVE HARD HAT AND WELDER'S HOOD

[75] Inventor: Julius T. Palumbo, Sulphur, La.

[73] Assignee: Arthur J. Planchard, Sulphur, La.; a part interest

[21] Appl. No.: 797,743

[22] Filed: May 17, 1977

[51] Int. Cl.² .............................................. A42B 3/00
[52] U.S. Cl. .......................................... 2/418; 2/424; 2/8
[58] Field of Search ................. 2/8, 10, 418, 419, 420, 2/417, 452, 424, 6, 421, 197, 12, 15

[56] References Cited

U.S. PATENT DOCUMENTS

| | | | |
|---|---|---|---|
| 2,272,833 | 2/1942 | Dockson | 2/8 |
| 2,658,200 | 11/1953 | Bowers, Sr. | 2/8 |
| 2,739,310 | 3/1956 | Frieder et al. | 2/418 |
| 2,801,420 | 8/1957 | Malcom, Jr. | 2/10 X |
| 2,983,923 | 5/1961 | Aileo | 2/418 |
| 3,241,154 | 3/1966 | Aileo | 2/419 |
| 3,329,968 | 7/1967 | Gordon | 2/8 X |

FOREIGN PATENT DOCUMENTS 682,753  11/1952  United Kingdom ...................... 2/452

Primary Examiner—Peter Nerbun
Attorney, Agent, or Firm—Clarence A. O'Brien; Harvey B. Jacobson

[57] ABSTRACT

A protective face and head apparel especially suited to the occupational needs of welders, the invention particularly comprises a hard hat with a scalloped lower edge and a head band assembly which includes an elastically deformable band for adjusting the fit of the head band assembly to the head of a user. A welder's hood or face shield is pivotally and resiliently supported from the hard hat with the pivot axis being related to the hard hat and hood so that the hood will be more evenly balanced above the head when pivoted upwardly to a generally horizontal position.

10 Claims, 6 Drawing Figures

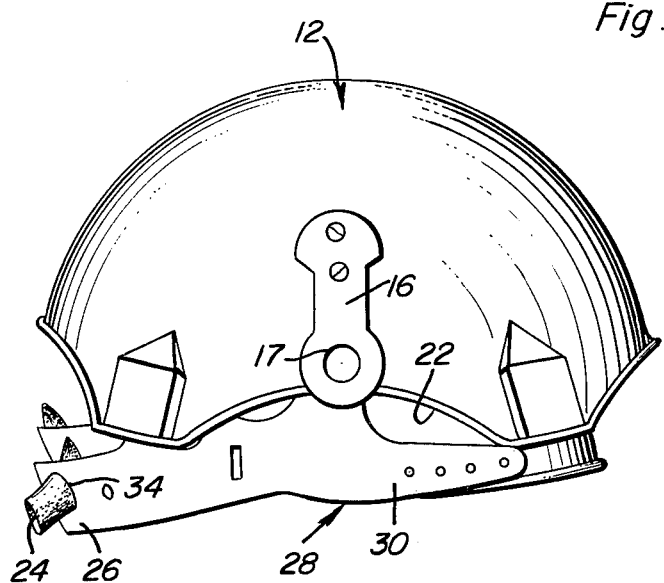
Fig. 2
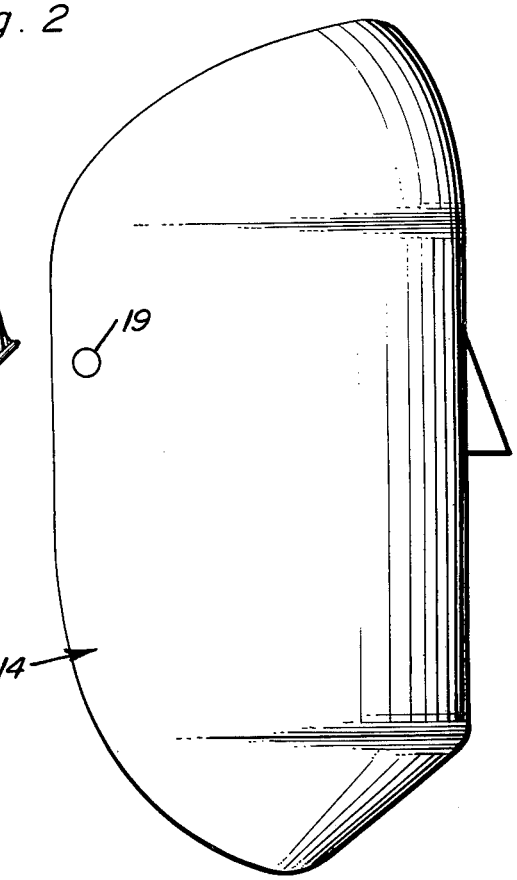
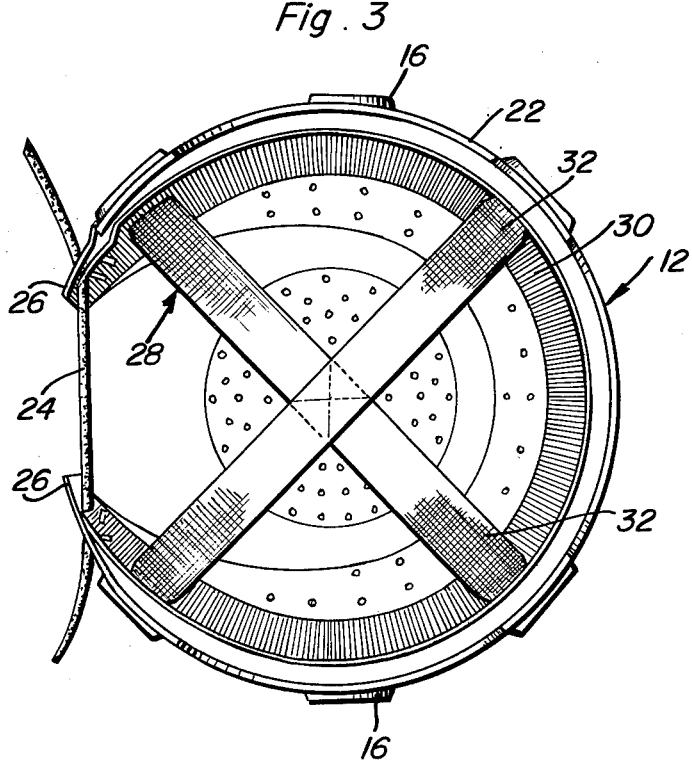
Fig. 3
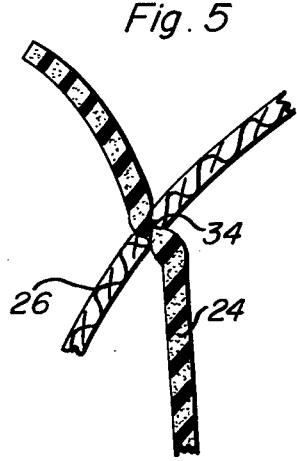
Fig. 5

PROTECTIVE HARD HAT AND WELDER'S HOOD

BACKGROUND AND SUMMARY OF THE INVENTION

The present invention relates to face and head protective apparel such as is normally used by welders, and the like, the invention particularly providing an elastically deformable band which is adjustable without removal of the apparel from the head of a user. Common practice in the construction industry and certain other fields requires the use of a protective headgear or "hard hat" by workers entering or performing work in hazardous areas. Welders or others requiring special facial protection must often work in these hazardous areas, a combination hard hat and face-protective shield being necessary to the usual practice of their trade. Prior hard hat/face shield combinations generally utilize lugs on the hard hat which couple with prongs on each side of the face shield, the hard hat and shield being separate, disconnectable structures. The face shield in such prior combinations can typically be tilted upwardly from the work position covering the face to a position wherein the lower edge of the face shield lies just above the line of vision of the wearer. The face shield thereby causes the combination to be "top heavy," i.e., to have a center of gravity located forward of the normal center of gravity of the hard hat and of the wearer, the combination thereby being susceptible to accidental displacement from the head of the wearer with normal head and body movement. When the wearer is working in high places, such as during construction of multi-story buildings or bridges, this tendency of prior hard hat/face shield combinations to "fall off" the head is not only disconcerting to the wearer but is also dangerous and wasteful of the worker's time.

Hard hat combinations of this type usually are provided with a suspension head harness and band disposed within the hard hat, the head band fitting over the cranial portion of the head. Such head bands are usually adjustable to fit the head size of a wearer. However, when perspiration or moisture from any other source causes the head band to become damp, the head band, and thus the hard hat, becomes loose on the head, thereby causing the hard hat to be susceptible to accidental displacement from the head. Although these prior art head bands can usually be adjusted when a poor fit develops during use, the act of adjustment requires that the hard hat be removed from the head. Work must then cease while the wearer uses both hands to adjust the head band in his hard hat. In many work situations, this adjustment process is difficult and even dangerous.

United States patents which disclose structure within the same field as the present invention and which are of interest in consideration of the patentability of the invention are as follows:

U.S. Pat. Nos. 1,182,367 — May 9, 1916 — Gravell; 2,272,833 — Feb. 10, 1942 — Dockson; 2,631,286 — Mar. 17, 1953 — Bowers; 2,926,357 — Mar. 1, 1960 — Edwards et al.; 3,047,876 — Aug. 7, 1962 — Malcom; 3,332,086 — July 25, 1967 — Simpson et al.; 3,763,495 — Oct. 9, 1973 — De Angelis.

The present invention provides a head band structure for hard hats and particularly for hard hat/face shield combinations, which head band can preferably be of the suspension type. The present apparatus also provides a face shield mountable on a hard hat for tilting movement from the working position to a position fully above the hard hat whereby the center of gravity of the combination is more nearly centered above the head of the wearer. Due to the combined advantageous effects of the present head band and face shield mounting structures, an apparatus is provided which can be securely worn and adjusted for git by a user even in high winds, in high places and in volumetrically, physiologically, and psychologically "tight" places. The present hard hat is also made lighter in weight by the provision of cut-away portions or "scallops" formed in edge portions thereof, the scalloped portions being so located as to allow adjustment of the usual skull cap or "welding cap" typically worn under the hard hat by a welder, the cap thereby being adjustable without removal of the hard hat from the head of the wearer.

The present head band preferably takes the form of a rubber tube or rope-like segment of elastically deformable material, the segment being held within holes disposed in spaced end portions of a standard head band. The segment of elastically deformable material, which can comprise a short length of surgical tubing, or the like, has a diameter which is slightly larger than the diameter of the holes when the segment is in a non-stressed, dimensionally stable conformation. In order to adjust the tightness of the head band, the elastic segment is longitudinally stretched and is thereby reduced in diameter transversely to the longitudinal axis of the segment. The segment can then be moved through at least one of the holes to either tighten or loosen the head band, and thus the hard hat or hard hat/face shield combination, on the head of a wearer. When the adjustment has been suitably completed, longitudinally directed stress on the segment is released to allow the segment to regain its original diameter, the segment then being gripped in the adjusted position by the pressure exerted by the holes. The head band can thus expand and contract with movement of the skin and muscles of the head. The user of the present head band can even bend over to a 90° or 120° position without the hard hat falling from the head. Further, the head band can be rapidly adjusted without removal of the hard hat from the head and with the use of only one hand.

It is, therefore, an object of the invention to provide an adjustable head band for a protective head apparel, at least a portion of which is formed of an elastically deformable material to allow rapid adjustment of the fit of the apparel on the head of a user.

It is a further object of the invention to provide a mounting structure for a protective head and face apparel, such as a hard hat and face shield, wherein the face shield can be pivotally tilted from a work position to a rest position surmounting the hard hat, the center of gravity of the combination when in the rest position being substantially centered directly above the head of a user.

It is another object of the invention to provide scalloped portions about lower perimetric edge portions of a hard hat having an adjustable head band to allow access to said head band and to associated structure disposed adjacent thereto.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 2 is an exploded view of the combination of FIG. 1;

FIG. 3 is a plan view of the underside of the hard hat;

FIG. 4 is a fragmental elevational view of the elastically deformable segment and adjacent ends of the head band taken along reference line 4—4 on FIG. 2;

FIG. 5 is a detail sectional view of the segment and head band taken substantially along section line 5—5 on FIG. 4; and, FIG. 6 is a detail sectional view of a preferred pivotal connection between the hat and the hood.

DESCRIPTION OF THE PREFERRED EMBODIMENTS

Figure 1:
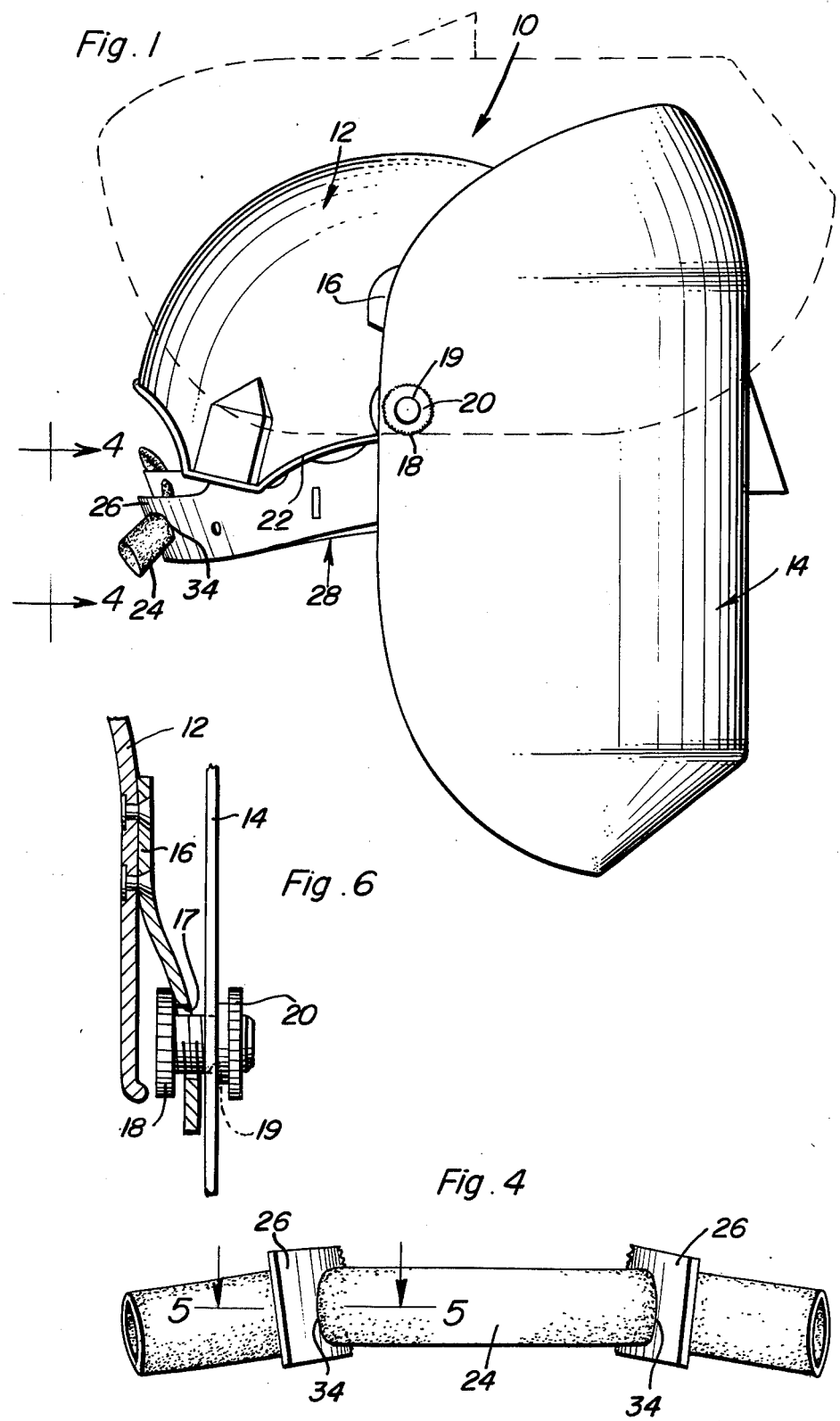
FIG. 1 is a side elevational view illustrating a hard hat and face shield or welder's hood combination having an elastically deformable segment provided in the head band located in the hard hat.

Referring now to FIGS. 1 and 2, a combination hard hat/face shield or welder's hood apparatus is seen at 10 to comprise a hard hat 12 formed of a rigid material such as is well-known in the art. The apparatus 10 further comprises a face shield 14 which can take a variety of shapes, such shields typically being arcuate in cross section and formed to wrap around or partially envelop the upper forward portion of the hard hat 12 and the face and throat of the wearer of the apparatus 10. The shield 14 can be opaque with a lens disposed therein opposite the eyes of the wearer, the lens being structured to admit a predetermined level of light. Alternately, the shield 14 or a lens disposed therein can be configured according to teachings in the prior art to become increasingly opaque with increasing levels of light from a source such as a welding arc or torch. As should now be understood, the hard hat 12 and face shield 14 can take differing forms and designs and remain useful in the practice of the present invention.

The hard hat 12 can be seen to have mounting tongues 16 fixed to each side thereof, the longitudinal axes of the tongues 16 being vertically disposed. Each tongue 16 has an aperture 17 formed at the lower portion thereof, a bolt 18 being insertable through the aperture 17 with the head of the bolt being disposed between the hat 12 and the tongue 16, a space being present between the hat 12 and tongue 16 since the tongues 16 extend at a slight angle from the hat 12. The bolts 18 extend through apertures 19 formed in spaced upper portions of each side of the face shield 14, the bolts 18 having mating nuts 20 fitting on distal ends thereof, the nuts 20 being tightened onto the bolts 18 to cause the shield 14 to be held in a desired spaced relation to the hat 12. The nuts 20 are tightened only enough to allow pivotal movement between the shield 14 and the hat 12. The face shield 14, due to the disposition of the apertures 19 near the rearmost edges of said shield and due to the location of the apertured tongues 16 near the lower peripheral edges of the hard hat 12, can be pivoted about the pivoted mounting structure thus described to a position surmounting the hard hat 12. The face shield 14 is capable of assuming a position over the hard hat 12 wherein the longitudinal axis of the shield 14, which axis is normally vertical when the shield 14 is in use, is disposed in a substantially horizontal orientation as shown in broken lines in FIG. 1. The apparatus 10 is thereby more nearly centered and balanced on the head of a wearer when the shield 14 is moved into a "rest" or non-work position. The tongues 16 can be preferably formed of a flexible metal fiber while the bolt 18 and nut 20 can be preferably formed of a rigid plastic material.

Referring still to FIGS. 1 and 2, the hard hat 12 is seen to have cut-away portions or scallops 22 formed in the lower peripheral edges thereof, one each of said scallops 22 being formed in the front and in the rear of the hard hat 12. One each of the scallops 22 is also formed in each side of the hat 12. The scallops 22 allow the wearer of the apparatus 10 to be able to adjust the soft cap (not shown) which is normally worn inside the hat 12 over the skull for comfort. The scallops 22 also cause the apparatus 10 to be lighter in weight and thereby easier to wear. Further, another important advantage of the scallops 22, at least the rear scallop 22, is that this cut-away portion of the hat 12 allows ready access to an elastically deformable band 24 which extends between spaced ends 26 of a suspension mounting 28 disposed within the hard hat 12. The suspension mounting 28 be more easily seen in FIGS. 2 and 3 to comprise an annular band-type strap or mount 30 having cross members 32 attached thereto and extending diametrically across the mount 30, the cross members 32 usually being attached to each other at their centers. The cross members 32 follow the contour of the head of a wearer and mount the hard hat 12 thereon in a suspension fashion such as is well-known in the art. The annular mount 30 is attached at suitable points to the interior surface of the hard hat 12 in a well-known manner. However, the annular mount 30 of the present invention is discontinuous at the rear portion thereof, the spaced ends 26 of said mount 30 each having a hole 34 formed therein which is of a diameter slightly smaller than the diameter or width of the elastic band 24.

As can be seen more readily in FIGS. 4 and 5, the elastically deformable band 24 is pinched and held within the holes 34 in the spaced ends 26 of the mount 30. The band 24 can take the form of a length of rubber tubing such as surgical tubing. Alternatively, the band 24 can be a solid piece of rubber or elastomeric material having a circular, rectangular, square, triangular, oblong, or other cross section. The exact structure of the band 24 can obviously take many forms in view of the function thereof. In particular, the band 24 is intended to be longitudinally deformable to reduce the effective diameter of the band within at least one of the holes 34, thereby to allow the band 24 to be pulled through one of the holes 34 in order to tighten the band 24 and thus the mount 30 on the head of the wearer. In other words, the band 24 can be stretched and thus tightened to bring the spaced ends 26 of the mount 30 closer together to cause the suspension mounting 28 to more closely conform to the contours of the head of a wearer of the hard hat 12. When longitudinally directed tension on the band 24 is released, the band 24 resumes its original diameter and is thus held in its adjusted position within the holes 34. Obviously, the band 24 can be adjusted to loosen as well as to tighten the fit of the hard hat 12 on the head of a wearer. The band 24 enables the suspension mounting 28 to expand and contract with the movements of the muscles and ligments in the neck and lower rear portion of the head of a wearer. Turning movements of the head as well as bending movements of the wearer can further be accommodated by the present structure without displacement of the hard hat 12 from the head of the wearer.

Due to the provision of the scallop 22 in the rear of the hard hat 12 and due to the ability to rapidly adjust the suspension mounting 28 provided by the elastically deformable band 24, the wearer can reach back with only one hand to adjust the band 24 during working operation when the mounting 28 becomes loose due to perspiration or other causes. Since the suspension mounting 28 is preferably mounted within the hard hat 12 with at least portions of the mount 30 disposed slightly below the scalloped lower peripheral edges of the hat 12, the head of a wearer is kept more cool than with prior art hat structures.

The foregoing is considered as illustrative only of the principles of the invention. further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. Head protective apparatus, comprising:

hat means for fitting over at least the external upper portions of the cranium of a wearer, the hat means being formed of a substantially rigid, protective material;

suspension mounting means attached to interior surfaces of the hat means for mounting the hat means on the head of a wearer, the suspension mounting means including an annular bandlike strap means which is discontinuous along a portion thereof, ends of the strap means at the discontinuous portion being spaced apart; and, an elastically deformable band disposed between the spaced ends of the strap means and adjustably connected thereto to lengthen and shorten that portion of the band lying between said spaced ends, the spaced ends of the strap means and the deformable band held therebetween being disposed outwardly of the hat means and exposed to be grasped at one end of the deformable band for adjustment of the fit of the suspension mounting means on the head of the wearer.

2. The apparatus of claim 1 wherein each of the spaced ends of the strap means has a single hole formed therein, the band being received within the holes and held therein.

3. The apparatus of claim 2 wherein the holes are of a diameter slightly smaller than the effective diameter of the band.

4. The apparatus of claim 1 wherein the hat means includes scalloped portions cut away from the body of the hat means along lower peripheral edges thereof, at least one of the scalloped portions surmounting the spaced ends of the strap means and the deformable band held therebetween to allow convenient access thereto.

5. The apparatus of claim 1 and further comprising mounting tongues affixed to the hat means and disposed immediately above the lower peripheral edges of the hat means on opposite sides thereof, the apparatus further comprising face shield means constructed to receive and encompass the front and forward portions of the lateral sides of the hat means, upper interior wall portions of said shield means encompassing said hat means having means pivotally connected to the mounting tongues to enable pivotal movement of the face shield means from a vertical working position to a horizontal position surmounting the hat means.

6. The apparatus of claim 5 wherein the mounting tongues extend downwardly at an angle from the lateral surfaces of the hat means, lower portions of the tongues being spaced from said surfaces of the hat means.

7. The apparatus of claim 6 wherein the tongues have apertures formed in the lower portions thereof which are spaced from the lateral surfaces of the hat means, and wherein the face shield means have apertures formed in each upper side thereof, the apparatus further comprising a bolt insertable through each pair of apertures in each tongue and in each side of the shield and a nut mating with each bolt to pivotally hold the shield onto the hat means.

8. The apparatus of claim 1 wherein the band comprises a length of hollow tubing formed of a material which is elastically deformable both longitudinally and transversely of its length.

9. The apparatus of claim 1 wherein the band comprises a solid length of a material which is elastically deformable both longitudinally and transversely of its length.

10. The apparatus of claim 4 wherein the strap means is discontinuous only at one portion thereof, the strap means being discontinuous at the rear of the suspension mounting means.

* * * * *